United States Patent [19]

Portman, Jr. et al.

[11] Patent Number: 4,799,378
[45] Date of Patent: Jan. 24, 1989

[54] PIEZOELECTRIC VISCOMETER

[75] Inventors: Joseph L. Portman, Jr., San Antonio; David J. Margraf, New Braunfels, both of Tex.

[73] Assignee: Alcor, Inc., San Antonio, Tex.

[21] Appl. No.: 79,684

[22] Filed: Jul. 29, 1987

Related U.S. Application Data

[63] Continuation-in-part of Ser. No. 931,660, Nov. 17, 1986, Pat. No. 4,697,657, which is a continuation-in-part of Ser. No. 789,515, Oct. 21, 1985, Pat. No. 4,623,030.

[51] Int. Cl.$^4$ ............................................. G01N 11/16
[52] U.S. Cl. ............................................. 73/54; 374/23
[58] Field of Search .................... 73/54, 64.1; 374/22, 374/23, 117

[56] References Cited

U.S. PATENT DOCUMENTS 3,201,970  8/1965  Beaugh et al. ...................... 374/23
4,558,588 12/1985  Beaudoin et al. ................... 73/54
4,602,505  7/1986  Kanda et al. ....................... 73/54

FOREIGN PATENT DOCUMENTS 602825  4/1978  U.S.S.R. ............................ 73/64.1
890150 12/1981  U.S.S.R. ............................ 73/54
911226  3/1982  U.S.S.R. ............................ 73/54

Primary Examiner—Stewart J. Levy
Assistant Examiner—Joseph W. Roskos
Attorney, Agent, or Firm—Gunn, Lee & Jackson

[57] ABSTRACT

A piezoelectric device is used to determine the viscosity of a fluid. A piezoelectric driver is resiliently attached to a base that is isolated from vibrations. A piezoelectric receiver and a probe are resiliently attached to the piezoelectric driver so that the receiver and probe move in response to motion of the piezoelectric driver, and the piezoelectric receiver gives an electric signal out proportional to motion of the system. The entire system is set to operate near the resonant frequency for the receiver/probe. By applying an oscillating sine wave voltage such as 140 hertz, to the piezoelectric driver, and immersing the probe first in a fluid of known high viscosity, and then in a fluid of known low viscosity, calibrated outputs are obtained from the piezoelectric receiver. Next by exchanging a fluid of unknown viscosity for the known fluids, a third output is obtained that represents the unknown viscosity.

14 Claims, 3 Drawing Sheets

FIG._3

PIEZOELECTRIC VISCOMETER

CROSS-REFERENCES TO RELATED APPLICATIONS

The present invention is a continuation-in-part of U.S. patent application Ser. No. 931,660, filed Nov. 17, 1987, now U.S. Pat. No. 4,697,657, which in turn was a continuation-in-part of U.S. patent application Ser. No. 789,515, for a Piezoelectric Ratio Weighing Device, filed Oct. 21, 1985, now U.S. Pat. No. 4,623,030.

BACKGROUND OF THE INVENTION

1. Field of the Invention

The present invention relates to viscosity measurement devices and, more particularly, to a piezoelectric device that determines the relative viscosity of a fluid whose viscosity is unknown.

2. Brief Description of the Prior Art

A fluid (liquid or gas) is a substance which undergoes continuous deformation when subjected to a sheer stress. When a fluid is set in motion, internal frictional forces act to oppose the motion of the fluid. This internal resistance to flow is known as viscosity. The theoretical viscosity of a fluid is defined as the force per unit area necessary to keep a plate, separated by a thin layer of fluid from a second plate, moving at a constant speed. If you measure the force required to keep the upper plate moving, you find that it is proportional to the area of the plates and to the ratio of the velocity of the upper plate to the distance separating the plates. This may be empirically written:

$$\frac{F}{A} = \eta \frac{v}{d}$$

The constant of proportionality $\eta$ (the Greek letter eta) is called the coefficient of viscosity. Through manipulation of the above equation, it can be seen that viscosity is in units of mass/(time-length). In the c.g.s. system, where the basic units of measurement are the centimeter, gram, and second, the unit of viscosity is the poise, where one poise equals one dyne-second per square centimeter. Viscosities are usually tabulated, however, in centipoises, being 1/100th of a poise.

There are several alternative measurements for viscosity. The "relative viscosity" of a fluid is the ratio of its viscosity to that of water (at 68° F.). Since the viscosity of water at 68° F. is very nearly 1 centipoise, the relative viscosity of a fluid is generally equal to its viscosity in centipoises. The kinematic viscosity of a fluid is its viscosity divided by its density. The c.g.s. unit of kinematic viscosity is called the stoke and equals one square centimeter per second.

Viscosity is an important useful property for any activity involving liquid flow. The viscosity of a liquid falls as temperature increases, and determining the temperature dependance of the viscosity of a fluid may be essential in assessing the suitability of certain oils or fuels. For example, the viscosity of aviation oils and fuels is critical because they must function efficiently at sub-zero temperatures. Also, information concerning the molecular weight and shape of organic molecules can be obtained from determinations of viscosity.

Viscosity is presently measured by three common methods. Each of these methods compares the viscosity of fluids rather than actually measuring the coefficient of viscosity. These instruments are known as viscometers. The first class, rotational viscometers, is the most important group of viscometric instruments. A container having a fluid therein is rotated around a stationary object, typically a coaxial cylinder that is suspended from a torsion wire. The deflection of the wire produced on a calibrated scale is proportional to the viscous drag.

In the second class of viscometers, a heavy object is allowed to fall freely through the viscous liquid, accelerating initially before it reaches a steady velocity known as the terminal velocity. This velocity, or conversely the time it takes for the object to fall through a predetermined distance, is measured and compared to other fluids with known viscosities. The Laray drop rod viscometer, in which a metal rod falls through an annular space filled with a liquid, is within this class.

The final class of viscometers measures the amount of time it takes for a predetermined volume of liquid to flow through a vertical capillary tube or an orifice. The term "Saybolt seconds", for example, refers to the time of efflux in a Saybolt viscometer.

Each of the above devices suffers from several disadvantages. First of all, those instruments require a relatively large amount of the fluid in order to measure viscosity. Secondly, they cannot detect minute changes in viscosity, which is especially useful in determining the freeze-point of jet fuels and such. Finally, the above viscometers do not allow for localized temperature fluctuations within the subject fluid. As discussed above, viscosity is critically dependent on temperature, and in some cases these fluctuations may result in false readings.

Applicants' invention is drawn to a specialized viscometer overcoming the above limitations through the use of piezoelectric technology. In the past, piezoelectric ceramics have been commonly used as receivers or drivers in electromechanical applications. A good descriptive article entitled "Piezoelectric Ceramics" by Eric A. Kolm, et al. published in *Mechanical Engineering*, February 1984, page 43, explains the operation of piezoelectric devices. However, it has never in any way been suggested that a piezoelectric type of device may be used to determine viscosity of a fluid. It would, therefore, be desirable and advantageous to devise a piezoelectric viscometer overcoming the above limitations.

SUMMARY OF THE INVENTION

Accordingly, the primary object of the invention is to provide a piezoelectric device capable of measuring the relative viscosity of known fluids.

Another object of the present invention is to provide such a piezoelectric viscometer capable of detecting minute changes in viscosity of the sample.

Yet another object of the invention is to provide a piezoelectric device capable of measuring the viscosity of relatively small samples of fluids.

Yet another object of the invention is to provide a piezoelectric viscometer capable of functioning as a freeze-point analyzer.

It is another object of the invention to provide such a piezoelectric viscometer which includes a special thermocouple to insure that all readings are taken at an exact temperature.

The foregoing objects are achieved in a piezoelectric device having a piezoelectric driver that vibrates in response to an AC signal, a piezoelectric receiver that gives an output signal in response to the vibrations, and a probe that is connected to the receiver at one end, the other end being placed in the fluid sample. The difference in amplitude between the driving frequency and the frequency at which the receiver vibrates within the fluid is related to the viscosity thereof. In operation, the system is first calibrated with various fluids of known viscosity. The system may also be used to determine temperature of a sample if the viscosity-temperature curve is already known.

DESCRIPTION OF THE PREFERRED EMBODIMENTS

Figure 1:
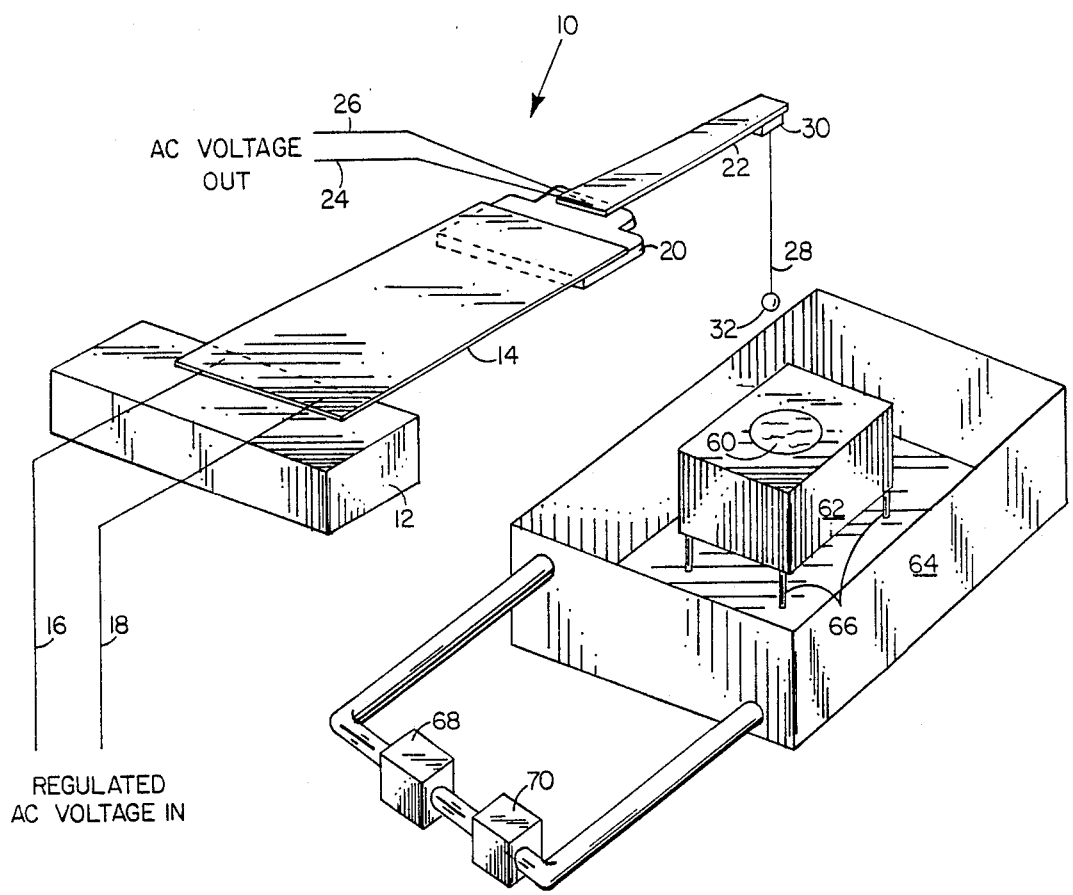
FIG. 1 is a perspective view of a piezoelectric viscosity measuring device.

Referring to FIG. 1, a simplified piezoelectric viscosity measuring device is illustrated generally by reference numeral 10. The piezoelectric viscometer has a base 12 which is the largest mass in the system. A piezoelectric driver 14 is attached to the base 12 by a suitable bonding material (not shown). The bonding material should be nonconductive so there will be no electrical conduction between the piezoelectric driver 14 and the base 12. A regulated AC voltage IN is connected to each side of the piezoelectric driver 14 by input lines 16 and 18 as shown.

With one end of the piezoelectric driver 14 being connected to the base 12, the opposite end of the piezoelectric driver 14 is bonded to a suitable dielectric material 20. Also connected to the dielectric material 20 is one end of a piezoelectric receiver 22. The piezoelectric receiver 22 has output lines 24 and 26 to give an AC voltage OUT during operation. Electrical isolation between piezoelectric driver 14 and piezoelectric receiver 22 is provided by dielectric material 20.

The opposite end of the piezoelectric receiver 22 is bonded to, but electrically isolated, from a probe 28 by a suitable dielectric material 30. Probe 28 is attached to receiver 22 at a right angle. The probe 28 terminates in a ball 32. A flat disk may be used in place of ball 32, but as the disk would create more turbulent flow, a ball is preferred. Because of the temperature dependency of viscosity measurements, probe 28 may also serve as a thermocouple. In this manner, the localized temperature of the fluid immediately surrounding the probe may be known.

Situated below probe 28 is the fluid 60 to be tested, contained in vessel 62. Vessel 62 is further situated within a receptacle 64 which is employed to control the temperature of fluid 60. Vessel 62 may be placed on stilts 66 to insure optimal temperature control. A pump 68 may be provided to circulate water or some other liquid within receptacle 64 and around vessel 62, the temperature of the water being appropriately controlled by a heating coil/condensor 70. Alternatively, if freeze point analysis is being performed, the receptacle 64 may be filled with dry ice or other frozen material, and the viscosity readings may be taken as the temperature drops.

By applying a regulated AC voltage IN to the piezoelectric driver 14, the piezoelectric driver 14 will begin to vibrate thereby causing the dielectric material 20 and the piezoelectric receiver 22 attached thereto to also vibrate. The bending action of the piezoelectric receiver 22 generates an AC voltage OUT over output lines 24 and 26. The vibration of the piezoelectric receiver 22 will, in turn, cause the probe 28 to oscillate in an essentially vertical path.

Unlike the inventions disclosed in the parent applications, the present invention is not a simple harmonic oscillator, but rather is a forced oscillator with damping. The general differential equation governing the motion of this system is:

$$m\ddot{x} + d\dot{x} + kx = F(t)$$

where,
m is mass,
d is the damping factor,
k is the modulus of elasticity,
$\ddot{x}$ is the second time derivative of location (acceleration),
$\dot{x}$ is the first time derivative of location (speed),
x is the location of the tip of the receiver, and
F(t) is the driving force as a function of time.

If the system is driven at or near the natural resonant frequency of the undamped system, the steady-state solution of the above equation is:

$$x = \frac{F(t)}{f\sqrt{c + d^2}}$$

where f is the driving frequency and c is a constant. It can, therefore, be seen that, if the damping factor is increased, the amplitude of the oscillations will decrease.

In our case, the damping factor is related to the viscosity of the unknown fluid. It has been experimentally proven that, when the piezoelectric viscometer 10 is driven at or near the natural frequency of the receiver/probe, the frequency vs. amplitude curve (power spectra) shifts in direct relation to the damping factor, resulting in a detectable change in amplitude at the driving frequency. By applying the device to liquids having known properties, this amplitude change may be correlated to a specific viscosity, and the device may thus be calibrated.

Figure 2:
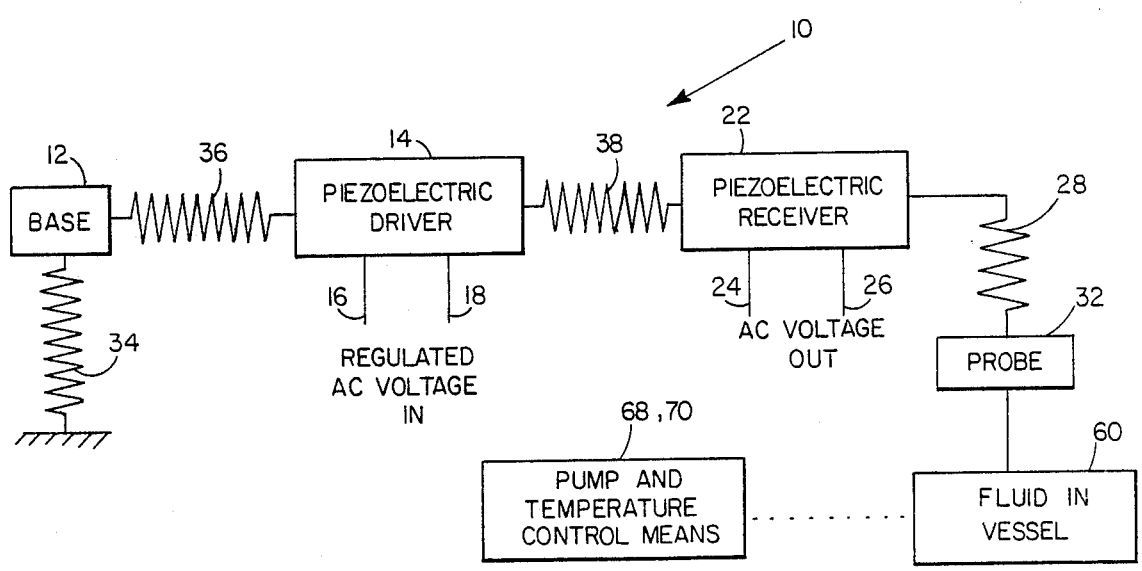
FIG. 2 is a schematic block representation of the piezoelectric viscosity measuring device illustrated in FIG. 1.

The piezoelectric viscometer 10 as illustrated in FIG. 1 is shown in a schematic block form in FIG. 2. The mass of base 12 is much larger than the mass of the piezoelectric driver 14, piezoelectric receiver 22, and probe 28. The spring 34 between the base 12 and the ground is fairly elastic and eliminates low frequency vibrations. The natural frequency of the base 12 is very low in comparison to the normal operating frequency range of the piezoelectric viscometer 10. The base 12 and spring 34 is designed to eliminate external shock and vibration.

The piezoelectric driver 14 induces the entire system to vibrate. By adjusting the frequency of the regulated AC voltage IN, the resonant frequency of the device 14 is determined. In the parent applications, the frequency was decreased slightly to insure that the device operated on the leading edge of the resonant frequency, but for the present invention, it is believed that setting the driver beyond the resonant frequency is preferable over setting it at the leading edge. The springs 36 and 38 on either side of the piezoelectric driver 14 are about equal and much weaker than the spring 34 attaching base 12 to the ground. The regulated AC voltage IN through input lines 16 and 18 causes an oscillation of the piezoelectric driver 14 of between 120-160 hertz. By experimentation, it has been determined that the frequency range between 120-160 hertz is where the resonant frequency normally occurred in the test models. However, it is important that the normal operating frequency range of the piezoelectric viscometer 10 not include the natural frequency of the piezoelectric driver 14 operating alone. Rather, the device should be set near the resonant frequency of the receiver/probe whose theoretical value is:

$$f_n = \frac{1}{2\pi\sqrt{\frac{m}{k}}}$$

This frequency may be determined by adjusting the frequency of the regulated AC voltage IN to give the maximum AC voltage OUT, which corresponds to maximum amplitude of the receiver/probe.

As the piezoelectric driver 14 vibrates and its vibrations are transmitted through spring 38 to the piezoelectric receiver 22, piezoelectric receiver 22 will give an AC voltage OUT through output lines 24 and 26 as a result of the mechanical tension/compression that takes place during the vibration. The AC voltage OUT may be processed and interpolated by a computer and is dependent on the damping force acting on probe 28.

Figure 3:
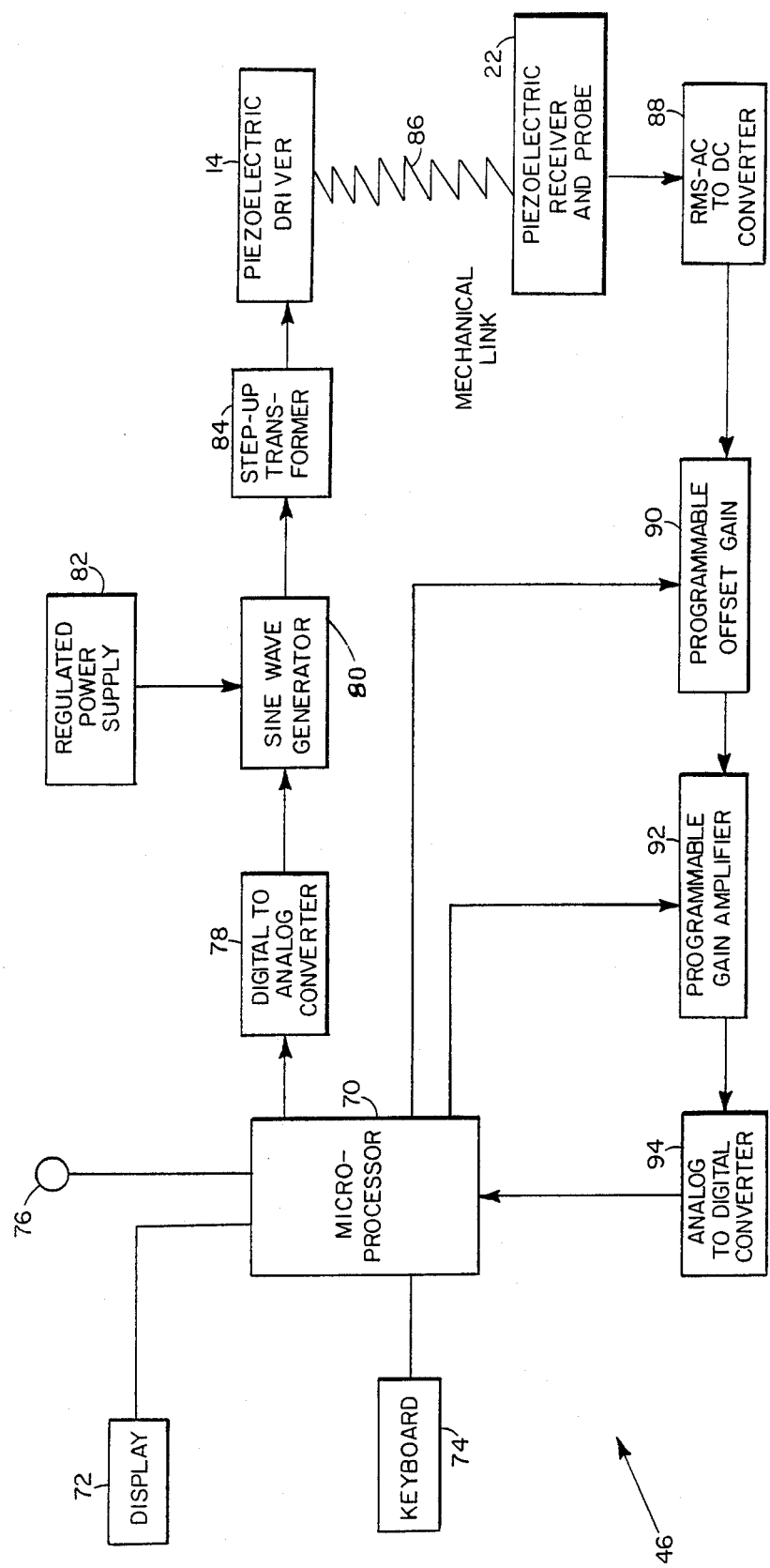
FIG. 3 provides a block diagram representation of part of the computer control of the present invention.

Referring now to FIG. 3, the computer control 46 is explained in more detail. The heart of the computer control 46 is a microprocessor 70. The microprocessor 70 has a display 72 that may be of any conventional type. While a typical cathode ray tube (CRT) may be used, it is envisioned that a more limited display of approximately four lines of forty digits using liquid crystal displays may be used to provide a limited visual indication. It is not necessary that the display 72 have the full display capabilities of a cathode ray tube. The language being used to communicate between the display 32 and the microprocessor 70 would typically be RS-232.

Also connected to the microprocessor 70 is a keyboard 74. Again, while a full-scale keyboard can be used, in the present invention a full-scale keyboard is not necessary. Therefore, the keyboard 74 as is presently envisioned for the current invention may simply be two or three sequencing push buttons that will give the very basic commands to the microprocessor 70. The sequencing push buttons would simply be a subset of the normal full keyboard for a microprocessor.

The microprocessor 70 may also provide an output to an extra terminal 76 or a host computer. The extra terminal 76 receives the same information as received by the display 72.

Referring now to the measuring provided by the computer control 46, the microprocessor 70 provides a digital signal to digital-to-analog converter 78. The digital-to-analog converter 78 converts the digital signal to analog form. The analog signal is then fed to sine wave generator 80. The sine wave generator 80 utilizes energy from a regulated power supply 82 and the analog signal from digital-to-analog converter 78 to give a variable frequency constant amplitude sine wave output. The frequency of the sine wave output may be varied by varying the digital signal from the microprocessor 70. The sine wave output is increased in voltage by step-up transformer 84. The stepped-up sine wave output from step-up transformer 84 is fed to the piezoelectric driver 14.

The sine wave voltage being fed to piezoelectric driver 14 causes the piezoelectric driver to vibrate. By a mechanical linkage 86, the piezoelectric driver 14 causes the piezoelectric receiver 22 to also vibrate. The vibration of the piezoelectric receiver 22 causes an AC voltage output therefrom which is fed to a root means square (RMS) AC to DC converter 88. In the RMSAC to DC converter 88, the AC signal is converted to a DC signal. The DC signal is fed to a programmable offset gain 90 which receives a feedback loop from the microprocessor 70. By adjustment of the programmable offset gain 90 through the microprocessor 70, a calibration control is provided for one end of the total piezoelectric viscometer 10. Calibration is performed by applying piezoelectric viscometer 10 to two different fluids of known viscosity. By testing a fluid of low viscosity, the zero point of the system may be established. The calibrated range is established by sampling a fluid of high viscosity, giving a full scale value. Processor 70 can then accomplish linearization, scaling, and display of relative viscosities of other fluids.

An output from the programmable offset gain 90 is fed to a programmable gain amplifier 92, which also has a feedback loop with the microprocessor 70. The programmable gain amplifier 92 provides the slope of the curve or what can be referred to as the span over which measurements would be taken. This defines the other end of the calibration. Assume, for example, the system is set to measure viscosities between 0.5 to 2.0 centipoise. By proper adjustment of the programmable gain amplifier 92, viscosities between 0.5 to 2.0 centipoise will cause the receiver output to be properly scaled near the resonancy frequency curve. It may be beneficial to have different sets of receiver/probes each having different associated resonant frequencies to insure accurate readings for different ranges of viscosities. For example, a highly viscous fluid, such as a thick oil, may overly dampen the vibrations of the receiver/probe. Therefore, a heavier receiver/probe with a slower resonant frequency may be necessary.

The output from the programmable gain amplifier 92 is fed through an analog-to-digital converter 94 back to the microprocessor 70. Within the microprocessor 70, the signal received from the analog-to-digital converter 94 is linearized by any of a number of methods. If the signal from the analog-to-digital converter 94 can be expressed in a mathematical formula, the microprocessor 70 can automatically convert the signal from the analog-to-digital converter 94 to equalize a certain viscosity as may be felt on the tip 32 of the probe 28. Another possibility is that the microprocessor 70 can contain in memory a chart or plotting of points that can be used to linearize the signal in direct proportion to the damping force felt on the tip 32 of the probe 28. This provides a very easy means for calibrating the piezoelectric viscometer 10 to known viscosity standards. Depending on ambient conditions and intended use, the piezoelectric viscometer 10 may need to be calibrated every day, week, or month.

Figure 4:
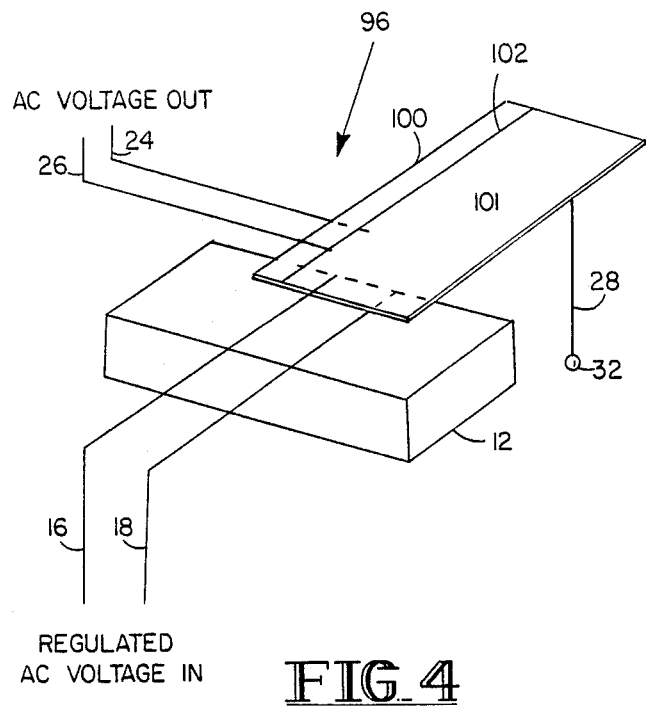
FIG. 4 is a perspective view of an alternative piezoelectric viscosity measuring device.
Figure 5:
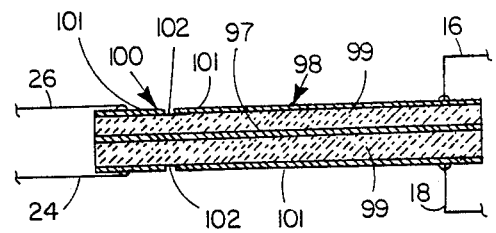
FIG. 5 is a cross-sectional view of the piezoelectric receiver and piezoelectric driver shown in FIG. 4.

It should be realized that the piezoelectric viscometer 10 as explained in connection with FIG. 1 is only one of many alternative configurations. Referring to FIG. 4, an alternative piezoelectric viscometer 96 is illustrated. The same base 12 as has been previously described will again be utilized. However, the piezoelectric driver 98 is now formed on the same ceramic sheet as the piezoelectric receiver 100 (see FIG. 6). Both the piezoelectric driver 98 and the piezoelectric receiver 100 are formed on a thin metal core 97 by cured ceramic layers 99 on either side thereof. A thin layer of nickel 101 is then deposited on the outside of the cured ceramic layers 99. However, by scoring the surface coating 101 (such as nickel) as represented by score mark 102, the piezoelectric receiver 100 is electrically isolated from the piezoelectric driver 98. Typically, a piezoelectric device will have a thin flat metal core 97 covered on both sides by a doped and cured ceramic 99. A thin layer of nickel 101 is deposited on the outside of the ceramic layers 99. The electrical connections are made to the layers of nickel 101. There may also be a protective coating around the entire device (not shown). Again, the piezoelectric driver 98 as well as the piezoelectric receiver 100 are bonded to, but electrically isolated, from base 12. Input lines 16 and 18 provide for the electrical connection to the piezoelectric driver 98. Likewise, output lines 24 and 26 provide the output signal from the piezoelectric receiver 100. The probe 28 again extends perpendicularly from receiver 22.

The piezoelectric connection as shown in FIG. 1 is sometimes referred to as a series connection and the connection as shown in FIG. 4 is sometimes referred to as a parallel connection. However, the alternative piezoelectric viscometer 96 as shown in FIG. 4 may be used equally as well as the embodiment shown in FIG. 1, except now the driver 106 will also resonate with the receiver/probe.

Figure 6:
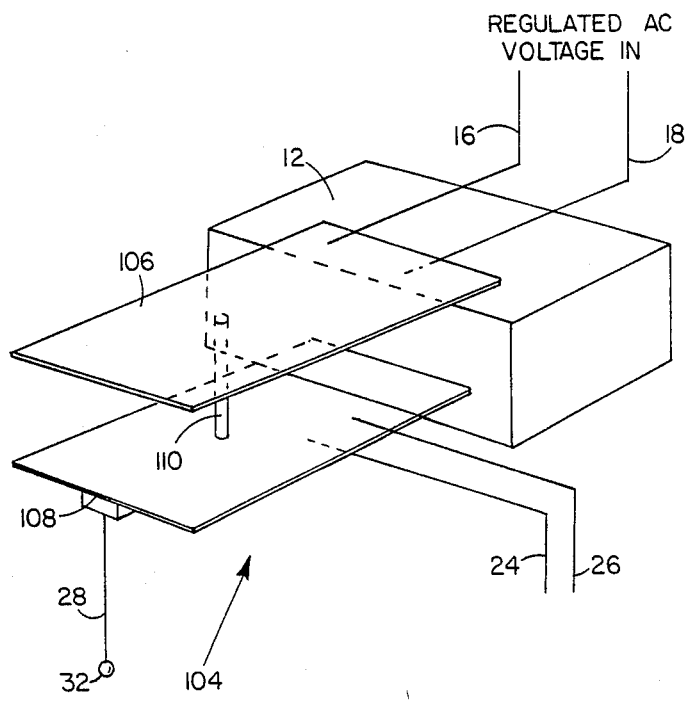
FIG. 6 is a perspective view of another alternative piezoelectric viscosity measuring device.

Referring now to FIG. 6, a second alternative piezoelectric viscometer 104 is illustrated. Again a piezoelectric driver 106 is electrically bonded to a base 12 by any suitable means. The piezoelectric driver 106, however, is electrically isolated from base 12. Again, input lines 16 and 18 provide for electrical connections to the piezoelectric driver 106. However, in this embodiment, the piezoelectric receiver 108 is bonded on one end to the base 12, but electrically isolated therefrom. The piezoelectric receiver 108 is mechanically connected to piezoelectric driver 106 by means of a sounding post 110. The sounding post 110 electrically isolates the piezoelectric driver 106 from the piezoelectric receiver 108, but transmits the vibratory signals therebetween. The output of the piezoelectric receiver 108 is received through output lines 24 and 26.

From the above illustrations, it should be clear that many different types of configurations for a piezoelectric viscometer can be used and not depart from the scope or spirit of the present invention. Also, it has been determined that many different types of probes can be used; however, in the preferred embodiment, the probe 28 is a quartz reed with the ball 32 being formed on the end thereof. It is preferable that any reed being used have a large length-to-diameter ratio but not so thin as to allow buckling.

It should also be realized that many different types of control functions can be provided by the computer control 46 with the electronic controls illustrated in FIG. 3 being representative as some of the controls that may be possible. All that is necessary is that (1) the resonant frequency be determined and the system set to operate near the resonant frequency, (2) the zero point be set by the programmable offset gain 90, and (3) the slope of the curve be set by the digital-to-analog converter 78 so that the system continues to operate near the resonant frequency of the system. It should be noted that the system can just as effectively operate when set on the leading edge of the resonant frequency, but engineers traditionally use the trailing edge.

There are many other functions that can be performed by the present invention other than determining viscosity of an unknown fluid. An example could be that the piezoelectric viscometer 10 is used as a thermostat. Where the viscosity-temperature curve of a fluid is well-known, an accurate measurement of viscosity results in a correlating measurement of temperature. The device has particularly useful application as a freeze-point analyzer. Also, for liquids of known viscosity, the piezoelectric viscometer could be used to measure the impurities within the liquid, since these impurities affect viscosity.

A further advantage of the piezoelectric viscometer 10 is that it is not dependent upon gravity. Therefore, the present device can be used as a type of scale that is suitable for operation in outer space. While gravity may have some effect on the piezoelectric viscometer 10, gravity is not essential to the operation of the device. All that is necessary is that the fluid be appropriately contained.

Although the invention has been described with reference to specific embodiments, this description is not meant to be construed in a limiting sense. Various modifications of the disclosed embodiments, as well as alternative embodiments of the invention, will become apparent to persons skilled in the art upon reference to the description of the invention. It is therefore contemplated that the appended claims will cover such modifications that fall within the true scope of the invention.

We claim:

1. A device for measuring the viscosity of a fluid comprising:
    a base;
    a piezoelectric driver anchored to, but electrically isolated from, said base;
    a piezoelectric receiver mechanically linked to, but electrically isolated from, said piezoelectric driver, for receiving vibrations therefrom;
    a probe mounted essentially perpendicularly to said piezoelectric receiver, for immersion in said fluid;
    an AC voltage source electrically connected to said piezoelectric driver, whereby said piezoelectric driver vibrates and transmits said vibrations to said piezoelectric receiver, said AC voltage having a frequency near the resonant frequency of said receiver; and
    means for receiving output signals from said piezoelectric receiver as vibrations are received from said piezoelectric driver, said output signal giving said viscosity of said fluid, said receiving means comprising:
        offset gain means to zero out said output signals when said probe is immersed in a first calibration fluid of known high viscosity; and
        gain amplifier means to maximize said output signals when said probe is immersed in a second calibration fluid of known low viscosity.

2. The device of claim 1 further comprising means to linearize said output signal with respect to viscosity.

3. The piezoelectric device of claim 1 further comprising means for controlling temperature of said fluid.

4. The piezoelectric device of claim 1 further comprising means for controlling temperature of said fluid.

5. The piezoelectric device of claim 1 wherein said piezoelectric driver, said piezoelectric receiver, and said probe each have first and second ends, said first end of said piezoelectric driver being anchored to said base, said second end of said piezoelectric driver being bonded to said first end of said piezoelectric receiver, and said second end of said piezoelectric receiver being bonded to said first end of said probe.

6. The piezoelectric device of claim 5 wherein said probe has temperature measuring means at said second end thereof.

7. The piezoelectric device of claim 1 wherein said piezoelectric driver and said piezoelectric receiver are formed from a single ceramic substrate having separate pairs of electrically isolated plates thereon, said single ceramic substrate being bonded on a first end to said base and on a second end to said probe.

8. The piezoelectric device as recited in claim 1 wherein said piezoelectric driver and said piezoelectric receiver are mounted in a parallel fashion to said base, soundpost means connecting said piezoelectric driver to said piezoelectric receiver to transmit vibrations therebetween.

9. A method of determining the viscosity of a fluid sample using a piezoelectric device consisting of the following steps:
(a) vibrating a piezoelectric driver that is mechanically linked to, but electrically isolated from, a piezoelectric receiver having a probe attached thereto, by supplying an AC voltage to said piezoelectric driver;
(b) setting said AC voltage near the resonant frequency of said piezoelectric receiver;
(c) first immersing said probe in a first calibration fluid of known high viscosity;
(d) zeroing an output signal from said piezoelectric receiver using offset gain means;
(e) second immersing said probe in a second calibration fluid of known low viscosity;
(f) maximizing said output signal from said piezoelectric receiver using gain amplifier means;
(g) third immersing said probe in said fluid sample;
(h) recording said output signal from said piezoelectric receiver; and
(i) correlating said recorded signal with said viscosities of said first and second calibration fluids to give said viscosity of said fluid sample.

10. The method of claim 9 further comprising the step of linearizing said output signals with respect to viscosity.

11. The method of claim 10 wherein said piezoelectric driver, said piezoelectric receiver, and said probe are mechanically isolated from external vibrations.

12. The method of claim 11 further comprising the step of maintaining said fluid sample at a constant temperature while recording said output signal.

13. A method of determining the temperature of a fluid sample having a known temperature-viscosity curve, using a piezoelectric device consisting of the following steps:
(a) vibrating a piezoelectric driver that is mechanically linked to, but electrically isolated from, a piezoelectric receiver having a probe attached thereto, by supplying an AC voltage to said piezoelectric driver;
(b) setting said AC voltage near the resonant frequency of said piezoelectric receiver;
(c) calibrating said piezoelectric device using a first calibration fluid of known high viscosity, and a second calibration fluid of known low viscosity, said known temperature-viscosity curve having viscosities within the range defined by said first and second calibration fluids;
(d) immersing said probe in said fluid sample;
(e) recording an output signal from said piezoelectric receiver;
(f) first correlating said output signal with viscosity of said fluid sample; and
(g) second correlating said viscosity of said fluid sample to said temperature of said fluid.

14. A device for measuring the viscosity of a fluid comprising:
a base;
a piezoelectric driver anchored to, but electrically isolated from, said base;
a piezoelectric receiver mechanically linked to, but electrically isolated from, said piezoelectric driver, for receiving vibrations therefrom;
a probe mounted essentially perpendicularly to said piezoelectric receiver, for immersion in said fluid;
an AC voltage source electrically connected to said piezoelectric driver, whereby said piezoelectric driver vibrates and transmits said vibrations to said piezoelectric receiver;
means for receiving output signals from said piezoelectric receiver as vibrations are received from said piezoelectric driver, said output signal giving said viscosity of said fluid; and
said piezoelectric driver, said piezoelectric receiver, and said probe each having first and second ends, said first end of said piezoelectric driver being anchored to said base, said second end of said piezoelectric driver being bonded to said first end of said piezoelectric receiver, and said second end of said piezoelectric receiver being bonded to said first end of said probe, said probe further having temperature measuring means at said second end thereof.

* * * * *